(12) United States Patent
Cassoni et al.

(10) Patent No.: US 8,349,121 B2
(45) Date of Patent: Jan. 8, 2013

(54) METHOD FOR PLACING A DESIRED LENGTH OF TAPE MATERIAL ONTO A MOVING WEB OF MATERIAL IN A TRANSVERSE ORIENTATION

(75) Inventors: Robert Paul Cassoni, Washington Township, OH (US); Terrence Curtis Hooker, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 280 days.

(21) Appl. No.: 12/754,815

(22) Filed: Apr. 6, 2010

(65) Prior Publication Data

US 2010/0252193 A1    Oct. 7, 2010

Related U.S. Application Data

(60) Provisional application No. 61/167,294, filed on Apr. 7, 2009.

(51) Int. Cl.
*B32B 37/00* (2006.01)
*B29C 65/00* (2006.01)
(52) U.S. Cl. .............. 156/299; 156/265; 156/297
(58) Field of Classification Search .......... 156/264, 156/265, 297, 299, 302, 362, 519, 520, 163, 156/229, 496, 552, 566, 569
See application file for complete search history.

(56) References Cited

U.S. PATENT DOCUMENTS

| | | | | |
|---|---|---|---|---|
| 4,726,874 | A * | 2/1988 | VanVliet | 156/495 |
| 5,296,080 | A * | 3/1994 | Merkatoris et al. | 156/496 |
| 6,139,004 | A | 10/2000 | Couillard et al. | |
| 6,227,541 | B1 | 5/2001 | Couillard et al. | |
| 6,719,031 | B2 | 4/2004 | Sawai | |
| 2003/0066609 | A1 | 4/2003 | Calvert | |
| 2003/0079330 | A1 | 5/2003 | Stopher et al. | |
| 2005/0072512 | A1 | 4/2005 | Shiomi et al. | |
| 2005/0133150 | A1 | 6/2005 | VanEperen et al. | |
| 2006/0201619 | A1* | 9/2006 | Andrews | 156/297 |
| 2007/0256777 | A1 | 11/2007 | Andrews | |

FOREIGN PATENT DOCUMENTS

GB    1 383 382 A    2/1974

OTHER PUBLICATIONS

PCT International Search Report, date mailed: Jul. 27, 2010, 14 pages.

* cited by examiner

*Primary Examiner* — John Goff
(74) *Attorney, Agent, or Firm* — Gary J. Foose

(57) ABSTRACT

An assembly and method for placing a desired length of tape material, fed as a moving continuous strip of tape material, onto a moving continuous web of material, wherein the orientation of the placed tape material is substantially perpendicular to the direction of movement of the moving continuous web of material.

3 Claims, 3 Drawing Sheets

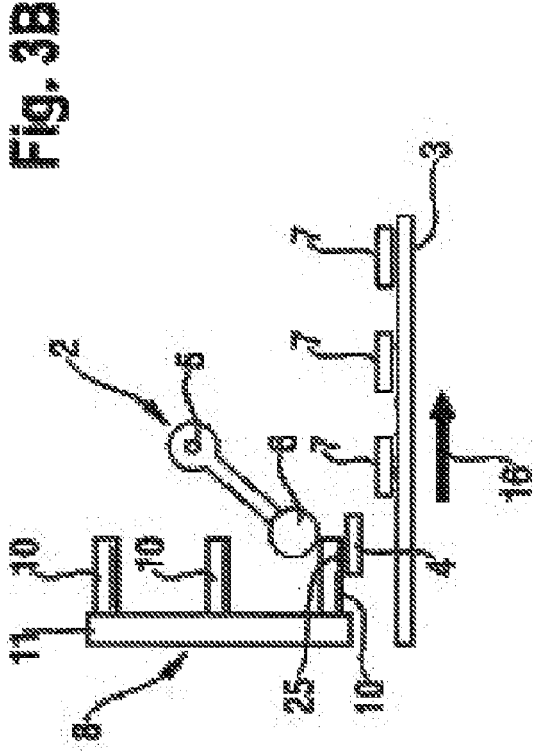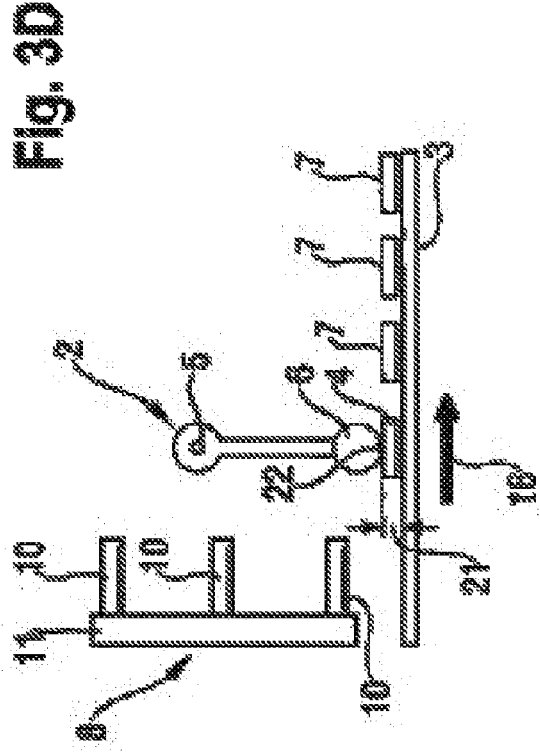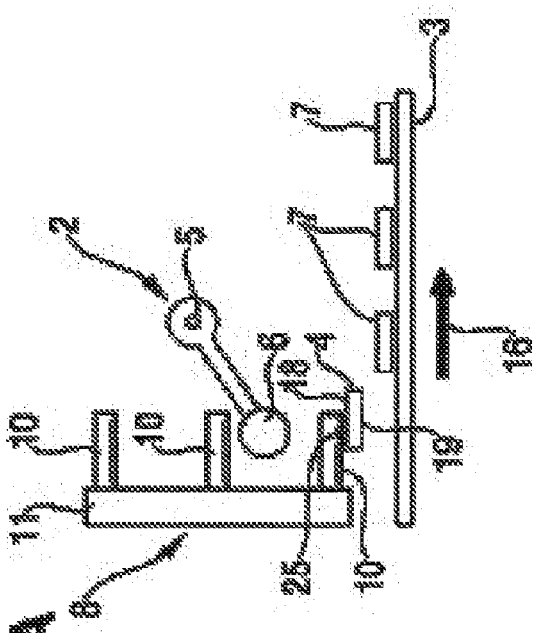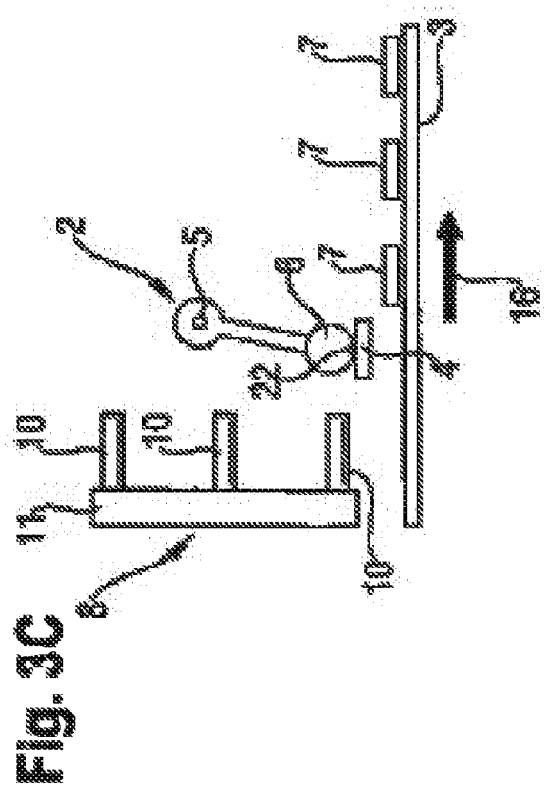

METHOD FOR PLACING A DESIRED LENGTH OF TAPE MATERIAL ONTO A MOVING WEB OF MATERIAL IN A TRANSVERSE ORIENTATION

CROSS REFERENCE TO RELATED APPLICATION

This application claims the benefit of U.S. Provisional Application Ser. No. 61/167,294, filed Apr. 7, 2009.

FIELD OF THE INVENTION

This invention relates to an apparatus and method for placing lengths of tape material fed as a moving continuous strip of tape material, in a transverse orientation onto a continuously moving web of material.

BACKGROUND TO THE INVENTION

The manufacture of a number of articles requires the addition of lengths of cut material to a moving web of material. Often, the material to be added to the moving web is in the form of long strips of tape material, usually stored on a parent roll. The tape material is fed into the apparatus, wherein desired lengths of the tape material are transferred onto the moving web of material.

Methods of placing lengths of tape material fed as a continuous strip are well known in the art. WO 03/037769 A1 is to an apparatus in which lengths of tape material are cut from the long strip and are subsequently transferred by a rotating member such that they are placed onto the moving web of material in the same orientation as the direction of movement of the web. The leading edge of the length of tape material is contacted first with the moving web and then the remainder of the strip is laid or rolled onto the surface of the web with the trailing edge contacting last.

A more complex situation arises when the length of tape material is to be placed in a transverse orientation to that of the direction of movement of the web of material. If the type of apparatus described in WO 03/037769 A1 (above) is used, then there is a tendency that the strips will be misaligned when placed onto the web. This is because the tape material is fed in a direction perpendicular to that of the moving web. Therefore, after the leading edge of the strip has been contacted with the moving web, by the time the trailing edge is contacted, the leading edge has already moved a distance in the same direction as the moving web. This also has the unfortunate effect of causing pleats or folds to be created in the moving web due to the leading edge being in contact with the web, but the trailing edge still being in contact with the transfer element of the apparatus, the pleat being formed as the leading edge moves away from the apparatus in a perpendicular direction, yet the trailing edge does not as it is still in contact with the transfer element, thus pulling the web of material towards the transfer element.

There exist apparatuses that can manipulate both the speed and direction of a desired length of tape material. The first is that of Couillard et al, U.S. Pat. No. 6,227,541 B1, which utilizes a multiple conveyer assembly for rotating and placing a strip of material on a substrate. However, such an apparatus is large, cumbersome, and requires a high level of maintenance. This also suffers from the further disadvantage that the speed of product throughput is also reduced as the tape material cannot simply be contacted leading edge first followed by trailing edge to the web as in WO 03/037769 A1, rather it requires careful placement manipulated by a number of sequential steps.

A second way of changing the direction of the length of tape material is achieved by Couillard et al, U.S. Pat. No. 6,139,004, the apparatus comprising a contour-changing conveyance surface. The apparatus utilizes a rotating transfer element which comprises rotating transfer surfaces. The transfer surface secures a strip of material that is running on a conveyer in the opposite direction to the web of material, and the transfer element then rotates to align the strip with a moving web of material. As it does this, the transfer surface also rotates about an axis which is perpendicular to the axis of the transfer element, such that the strip is positioned so it is placed in a transverse orientation on the moving web of material.

A problem with such an apparatus is that in at least one embodiment, the transfer element is in contact with both the conveyer carrying the strip and the moving web of material. Such an embodiment would require the strip material and web of material to have matched speeds. This then limits the frequency of placement of the strip material onto the web by the length of the strip material. In order to change the frequency of placement of the strip material, the diameter of the transfer element would need to be altered.

Another problem with the above mentioned technologies is that they require the strip of tape material to be handled on both sides during the transfer process; usually because the tape material is presented to the transfer element on a conveyer. This is inconvenient, especially if it is desired that at least one side comprise an adhesive substance.

A further problem is that current technologies require complex manipulation to re-orientate the desired length of tape material during the transfer process. Complex apparatuses tend to suffer increased mechanical wear, in turn increasing maintenance costs. This can result in lower rates of product throughput.

There is a need in the art to provide an apparatus for placing lengths of tape material in a transverse orientation onto a moving web of material, wherein only one side of the length of tape material needs to be handled by the apparatus during the transfer process. There is a further need in the art for an apparatus for placing lengths of tape material in a transverse orientation onto a moving web of material, wherein the frequency of placement of the tape material onto the web is independent of the length of the tape material. There is a further need to provide a cheap, simple, low maintenance apparatus that has a high product through-put capability.

The present invention offers an apparatus and method for placing a desired length of tape material moving in a first direction onto a moving web of material, moving in a second direction, in a transverse orientation, wherein the desired length of tape material is only handled on one side during the transfer process. Furthermore, the placement frequency of the desired length of tape material onto the moving web of material is independent of the length of the desired length of tape material when the tape material and the web of material are moving at matched speeds. The apparatus is also simple, cheap and of low maintenance comprising few complex components.

SUMMARY OF THE INVENTION

A first aspect of the present invention is an apparatus 100 for applying desired lengths of tape material 4, the tape material fed as a moving continuous strip 1, to a moving continuous web of material 3, comprising;

a moving continuous strip of tape material 1 comprising desired lengths of tape material 4, and wherein the desired lengths of tape material 4 are presented in a first direction 15;

a paddle 2 which rotates about an axis 5, comprising at least one paddle transfer surface 6;

a moving continuous web of material 3, moving in a second direction 16, the second direction being oriented at an angle 17 of 90°+/−30°, preferably 90°+/−20°, more preferably 90°+/−15°, even more preferably 90°+/−5°, most preferably 90°+/−1° with respect to the first direction 15;

wherein the paddle 2 transfers, on the paddle transfer surface (6), the desired length of tape material 4 provided in the first direction 15, onto the moving continuous web of material (3) moving in a second direction 16.

A second aspect of the present invention is a process for transferring a desired length of tape material 4 from a moving continuous strip of tape material (1) being fed in a first direction 15, to a moving continuous web of material 3 moving in a second direction 16, comprising the steps of;

providing the desired length of tape material (4) in a first direction 15;

rotating a paddle 2 about an axis 5 so that a first side of the desired length of tape material 4 is brought into contact with a transfer surface of the paddle 6;

removably securing the first side 17 of the desired length of tape material 4 to the transfer surface of the paddle 6;

further rotating the paddle 2 comprising the first side 18 of the desired length of tape material 4 being removably secured to the transfer surface of the paddle 6, about the axis 5, so that a second side 19 of the desired length of the tape material 4 is brought into contact with the moving web of material 3;

unsecuring the first side 18 of the desired length of tape material 4 from the transfer surface of the paddle 6;

wherein the first direction 15 is oriented at an angle 17 of 90°+/−30°, preferably 90°+/−20°, more preferably 90°+/−15°, even more preferably 90°+/−5°, most preferably 90°+/−1° with respect to that of the second direction 16.

BRIEF DESCRIPTION OF THE DRAWINGS

FIG. 3A-D represents a series of steps for transferring a desired length of tape material 4 from a moving continuous strip of tape material 1 onto a moving continuous web of material 3, such that the desired length of tape material 4 is secured to the moving continuous web of material 3 in a transverse orientation 7.

DETAILED DESCRIPTION OF THE INVENTION

Figure 1:
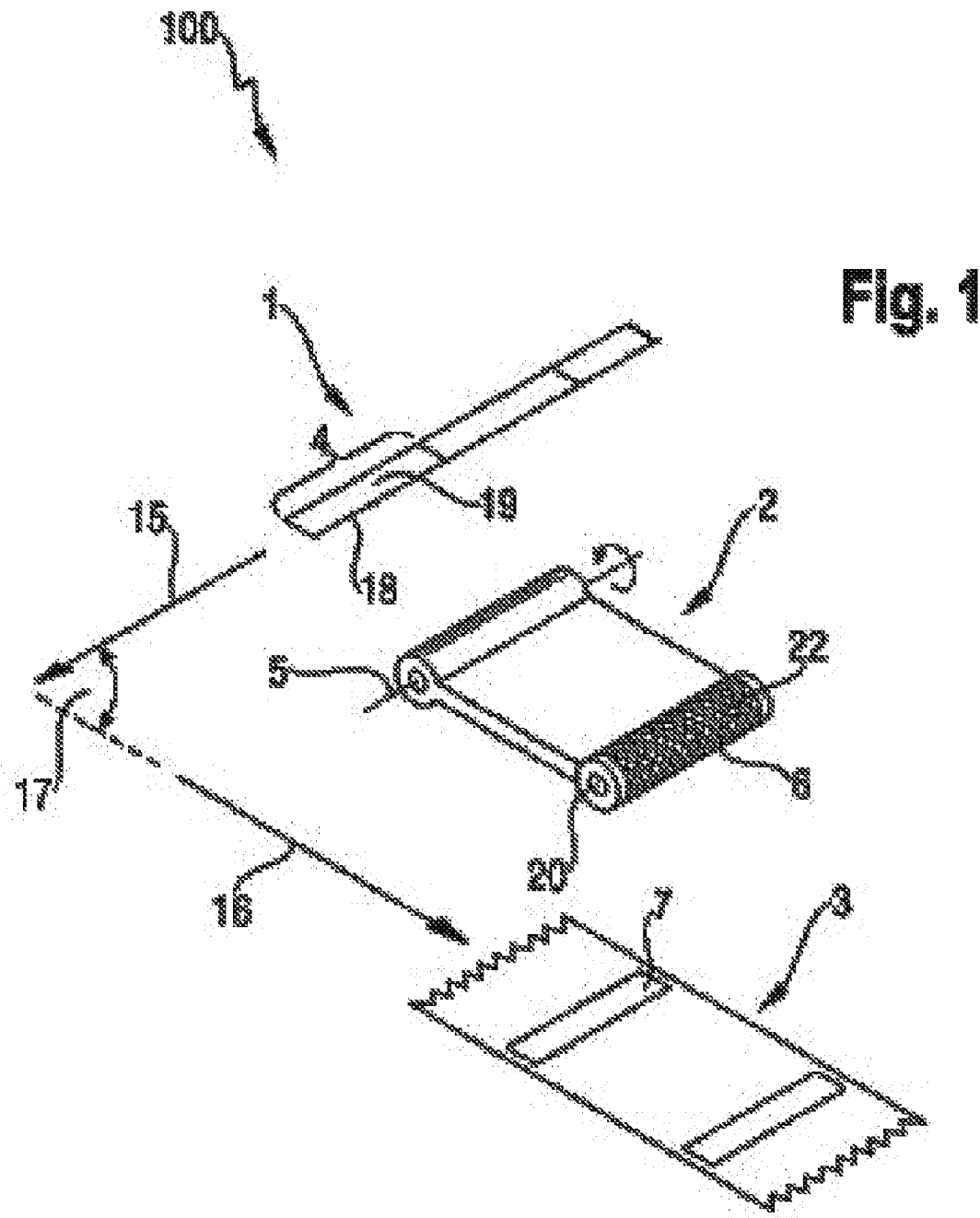
FIG. 1 shows an exploded diagram of the apparatus 100 of the present invention which comprises, a moving continuous length of tape material 1 segmented into desired lengths of tape material 4, a paddle 2, and a moving continuous web of material 3.

The present invention provides an apparatus 100 and method for placing a desired length of tape material 4, fed as a moving continuous strip of tape material 1, onto a moving continuous web of material 3, wherein the orientation of the placed tape material 7 is substantially perpendicular to the direction of movement of the moving continuous web of material 3.

By 'removably secured' we herein mean the desired length of tape material 4 is secured in place but not necessarily in a permanent manner. It should be understood that it is the intention for the desired length of tape material 4 to be secured such that a particular operation of the apparatus 100 is achievable but that it may then be unsecured and removed for the next step.

By 'substantially perpendicular' we herein mean the first direction 15 of movement of the tape material 1 can be oriented at an angle 17 of 90°+/−30°, preferably 90°+/−20°, more preferably 90°+/−15°, even more preferably 90°+/−5°, most preferably 90°+/−1° with respect to the second direction 16 of movement of the moving continuous web of material 3. It is intended that the positioning of the desired length of tape material 4 presented in a first direction 15 correlates to the intended transverse orientation of placement of the desired length of tape material 7 onto the moving continuous web of material 3.

By 'adhesive substance' we mean a substance which exhibits adhesive properties enabling it to bond one substrate to another.

The Apparatus

FIG. 1 is an exploded diagram of the apparatus 100. It comprises a moving continuous strip of tape material 1, which is moving in a first direction 15 as indicated by the arrow, a paddle 2 and a moving continuous web of material 3, which is moving in a second direction 16 as indicated by the arrow. The first direction 15 of movement is substantially perpendicular to the second direction of movement 16.

The moving continuous strip of tape material 1 comprises desired lengths of tape material 4. The moving continuous strip of tape material 1 can be segmented so as to comprise desired lengths of tape material 4 using any suitable method, preferably selected from the group comprising cutting, slicing, perforating, shearing, slashing, guillotining, dicing, dissecting, scoring, slitting, snipping and combinations thereof.

The moving continuous strip of tape material 1 can be any suitable material, preferably selected from woven materials, non-woven materials, films, webs, flexible membranes and combinations thereof. The moving continuous strip of tape material 1 can be flexible or rigid. The moving continuous strip of tape material 1 comprises a first side 18 and a second side 19. The first side 18 can comprise further elements, preferably selected from the group comprising hooks, adhesive substances, discrete rigid objects, discrete flexible objects and combinations thereof. In one embodiment, the first side 18 is essentially free of any further element. In a preferred embodiment, a first side 18 of the moving continuous strip of tape material 1 comprises hooks and a second side 19 comprises an adhesive substance. The hooks can be manufactured from any material capable of generating a hook structure, preferably selected from the group comprising metals, cloths, plastics and combinations thereof. In a preferred embodiment, the hooks are manufactured from plastic, more preferably from polyethylene. In another embodiment, a first side 18 of the continuous strip of tape material 1 comprises an adhesive substance, and the second side 19 comprises an adhesive substance.

The paddle 2 comprises an axis 5 around which it can rotate and at least one transfer surface 6. In a preferred embodiment, the paddle comprises 2 transfer surfaces orientated on opposite sides to the axis 5. Desired lengths of tape material 4 are transferred on the transfer surface 6 from the moving continuous strip of tape material 1 to the moving continuous web of material 3, such that the desired lengths of tape material 4 are placed in a transverse orientation 7 to the direction of movement of the moving continuous web of material 3. The desired length of tape material 4 is removably secured to the transfer surface 6 using any suitable method, preferably selected from the group comprising vacuum suction, adhesive, clamping, hooking, gripping, and combinations thereof. In a preferred embodiment, the desired length of tape material 4 is removably secured to the paddle transfer surface 6 using vacuum suction. The paddle transfer surface 6 may also comprise other elements that increase friction on the paddle transfer surface and help minimize sliding of the desired length of tape material 4 across the paddle transfer surface 6. Elements that improve grip and help minimize sliding are preferably selected from the group comprising rubber based materials, macro mechanical features such as pins, bumps or nubs, strips of a mating loop material that corresponds to hooks on the surface of the desired length of tape material 4 and combinations thereof. In all embodiments, the paddle 2 only contacts one side of the desired length of tape material 4.

Rotation of the paddle 2 about the axis 5 can be driven via any suitable means, preferably selected from the group comprising servo controlled motor and drive, planetary set of gears, synchronous and unsynchronous belts, chains, cams, cables, pneumatics, hydraulics and combinations thereof. In a preferred embodiment, the paddle 2 is rotated about the axis 5 via a servo controlled motor and drive. In another embodiment the paddle 2 is rotated about the axis 5 via a planetary set of gears.

The paddle 2 can rotate through 360°, hereinafter called the 360° paddle rotation. The paddle 2 can rotate in a clockwise or an anticlockwise direction. Over the course of a 360° paddle rotation, the orientation of the paddle transfer surface 6 can be varied. The orientation of the paddle transfer surface 6 comprising a desired length of tape material 4, a first side 18 of the desired length of tape material 4 being removably secured to the transfer surface 6, can vary during a 360° paddle rotation such that the second side of the desired length of tape material 4 becomes substantially parallel in orientation to the moving continuous web of material 3 at the point of transfer of the desired length of tape material 4 from the paddle transfer surface 6 to the moving continuous web of material 3. Once the desired length of tape material 4 has been deposited onto the moving continuous web of material 7, the paddle transfer surface 6 further varies its orientation as the paddle 2 continues through the 360° paddle rotation so that it is orientated in such a manner as to contact the next desired length of tape material 4 presented in a first direction 15. Preferably, the paddle transfer surface 6 is orientated such that it is substantially parallel to the desired length of tape 4 at the point the desired length of tape material 4 is transferred to the paddle transfer surface 6.

In a preferred embodiment, the paddle transfer surface 6 comprises an axis 20 around which it can rotate. Rotation of the paddle transfer surface 6 around its axis 20 allows it to vary its orientation. In a preferred embodiment, a series of gears (helical/spur) are used to provide a rotational input to the paddle transfer surface 6 rotating about its axis 20. In another embodiment, a rotational input to the paddle transfer surface 6 rotating about its axis 20 is accomplished using a twin power synchronous timing belt. In yet another embodiment, to achieve a rotational input to the paddle transfer surface 6 rotating about its axis 20, a servo-stepper motor is used. Preferably, the axis 20 of the paddle transfer surface 6, runs in a parallel orientation to that of the paddle axis 5.

In a preferred embodiment, the transfer surface 6 comprises one or more vacuum ports 22, wherein the desired length of tape material 4 is removably secured using vacuum suction.

The moving continuous web of material 3 can be any suitable material, preferably selected from the group comprising woven, non-woven material, extruded material, polyethylene film and combinations thereof. In a preferred embodiment, the moving continuous web of material 3 is polyethylene film.

The moving continuous web of material 3 can be fed in the second direction 16 using any suitable method as is generally known in the art, preferably selected from the group comprising conveyer belt, s-wrap roller drive, nip roller drive and combinations thereof.

The moving continuous strip of tape material 1 can be stored in a place located away from the apparatus 100 and then fed from the storage area to the apparatus 100. In one embodiment the moving continuous strip of tape material 1 is stored on a parent roll, the parent roll resting on a free rolling bearing. It can then be fed into the apparatus 100 using methods generally known in the art, such that a desired length of tape material 4 is presented in a first direction 15.

The moving continuous strip of tape material 1 can be sectioned into the desired lengths of tape material 4 at any suitable time before the desired length of tape 4 is presented in a first direction 15. Non-limiting examples include, the moving continuous strip of tape material 1 could be pre-perforated before it is stored, or could be sectioned by cutting as it is fed into the apparatus 100 from the storage means.

Figure 2A:
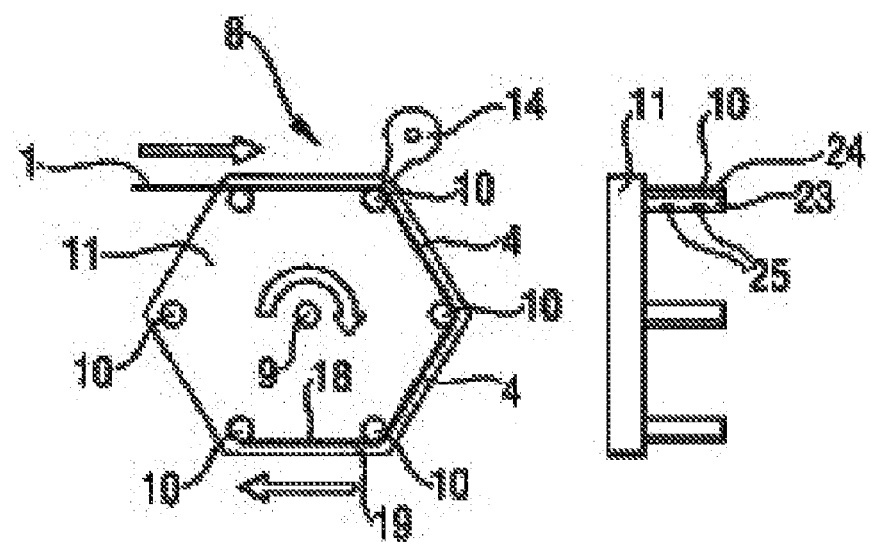
FIG. 2A shows a preferred embodiment of an anvil 8 comprising a central axis 9, a number of temporary securing points 10, a rotating knife 14, and a moving continuous strip of tape material 1.
Figure 2B:
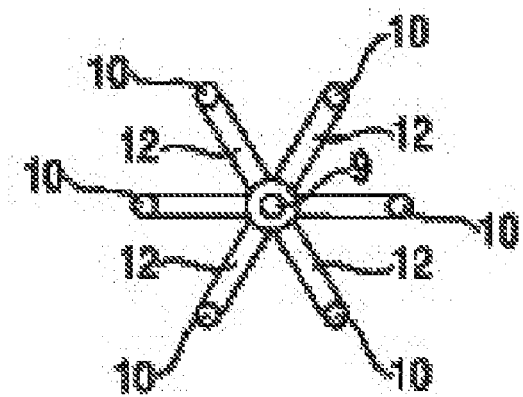
FIG. 2B is another embodiment of the anvil.

In one embodiment, the moving continuous strip of tape material 1 is fed from the parent roll to the apparatus 100, and a desired length of tape material 4 presented in a first direction 15 by means of an anvil 8. The anvil 8, in the context of the present invention, feeds the moving continuous strip of tape material 1 from the parent roll and presents a desired length of tape material 4 in a first direction. FIG. 2A depicts a preferred embodiment of the anvil 8. The anvil 8 comprises a central rotating axis 9 around which a number of temporary securing points 10 are arranged. Any suitable means can be used to arrange the temporary securing points 10 around the central axis 9. For example, in one embodiment they are arranged on an hexagonal backplate 11 which rotates around the central axis 9; however this a non-limiting shape. Those skilled in the art will recognize other suitable shapes that can be used as a backplate 11. In one embodiment, the backplate 11 is circular in shape. In a further embodiment, no backplate 11 is used, rather, the temporary securing points 10 are positioned at the end of spokes or arms 12 which are arranged around the central axis 9 as depicted in FIG. 2B.

The anvil 8 can be rotated about the axis 9 via any suitable means, preferably selected from the group comprising servo controlled motor and drive, planetary set of gears, synchronous and unsynchronous belts, chains, cams, cables, pneumatics, hydraulics and combinations thereof. In a preferred embodiment, the anvil 8 is rotated about the axis 9 via a servo controlled motor and drive. In another embodiment, the anvil 8 and paddle 2 are mechanically coupled and simultaneously rotated about their respective axes 5,9 via a single servo controlled motor and drive. In a further embodiment, the anvil 8 and paddle 2 are mechanically coupled and simultaneously rotated about their respective axes 5,9 via a single servo controlled motor and drive, wherein the anvil 8 and paddle 2 rotate at different rotational velocities achieved by suitable velocity profile control means, preferably selected from the group comprising non-linear gearsets comprising elliptical gears, pulleys or the like, Geneva or indexing mechanism and combinations thereof.

Preferably, the axis of rotation of the paddle is oriented at an angle 17 of 90°+/−30°, preferably 90°+/−20°, more preferably 90°+/−15°, even more preferably 90°+/−5°, most preferably 90°+/−1° with respect to the axis 9 of rotation of the anvil 8.

Figure 2C:
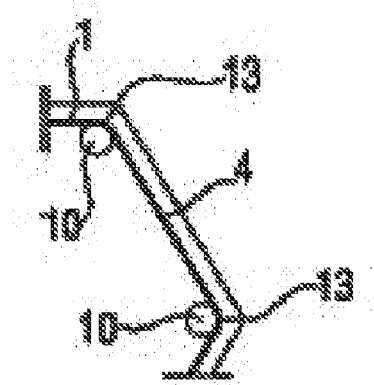
FIG. 2C depicts the interaction between desired lengths of tape material 4 and the temporary securing points 10 of the anvil 8.

The temporary securing points 10 are positioned such that each desired length of tape material 4 is removably secured at each end between the temporary securing points 10. Therefore, the temporary securing points 10 are arranged such that a desired length of tape material 4 is secured at the point it joins the next desired length of tape material 13 as depicted in FIG. 2C. Thus the desired length of tape material 4 is removably secured in such a way as to be held between the temporary securing points 10. Also, only one side of the desired length of tape material 4 is in contact with the anvil 8.

The moving continuous strip of tape material 1 is fed around the anvil 8 and removably secured by the temporary securing points 10. Securing can be achieved using any suitable method, preferably selected from the group comprising vacuum suction, adhesive, clamping, hooking, gripping and combinations thereof. Each temporary securing point 10 comprises one or more sections. In a preferred embodiment, the temporary securing points 10 are comprised of a first section and a second section, wherein the first section 23 comprises a cutting surface and the second section 24 comprises a holding section. In a preferred embodiment, the first section 23 comprises a cutting surface and the second section 24 comprises one or more vacuum suction ports 25.

In a preferred embodiment, the moving continuous strip of tape material 1 is segmented into desired lengths of tape material 4 by a servo-driven rotating knife 14. The servo-driven rotating knife 14 rotates in synchronization with the anvil 8 so that the servo-driven rotating knife blade 14 hits the anvil 8 at a desired pitch such that the moving continuous strip of tape material 1 being fed around the anvil 8 is cut into desired lengths of tape material 4. In a more preferred embodiment, the servo-driven rotating knife 14 rotates in synchronization with the anvil 8 so that a knife blade 14 hits a temporary securing point 10 cutting the moving continuous strip of tape material 1 being fed around the anvil 8 into desired lengths of tape material 4. Each of these desired lengths of tape material 4 is then removably secured at each end between the temporary securing points 10 as described above. Therefore, the temporary securing points 10 are positioned such that desired lengths of tape material 4 are removably secured at each end between the temporary securing points 10. In a preferred embodiment, the holding section of the temporary securing point 10 restricts the tape 1 from moving during the cutting process occurring on the cutting surface of the temporary securing point 10.

In one embodiment the servo-driven rotating knife 14 diameter is the same as the anvil 8 diameter and both the knife 14 and the anvil 8 are driven at the same rotational velocity. Preferably, the servo-driven rotating knife 14 and the anvil 8 have matched tangential velocities at the time the servo-driven rotating knife 14 cuts the moving continuous strip of tape material 1 into desired lengths of tape material 4. In a preferred embodiment, the diameter of the servo-driven knife 14 is smaller than the diameter of the anvil 8 and the rotational velocity of the servo-driven rotating knife 14 is servo profiled, so that the servo-driven rotating knife 14 and anvil 8 tangential velocities are equal at the time the servo-driven rotating knife 14 cuts the moving continuous strip of tape material 1 into desired lengths of tape material 4. Matched tangential velocity should be maintained within +/−15° of the cutting centerline. Those skilled in the art will recognize suitable means known in the art to achieve this. Having matched tangential velocities of the servo-driven rotating knife 14 and the anvil 8 at the point the servo-driven rotating knife 14 cuts the moving continuous strip of tape material 1 into desired lengths of tape material 4, prevents 'scrubbing' of the servo-driven rotating knife 14 along the anvil surface. By "scrubbing" we herein mean the relative motion of the rotating knife blade 14 across the anvil 8 or other surface. In other words, this is a sliding motion of the knife blade 14 across the anvil 8 or other surface which can limit the knife or anvil/other surface operational lifespan, as well as affect the quality of the cut material.

Those skilled in the art will recognize suitable means to vary the length of the desired lengths of tape material 4. In one embodiment, the length of the desired length of tape material 4 is varied by changing the diameter of the anvil 8. A number of 'changeout' anvils 8 of varying diameter can be used to achieve varying lengths of desired lengths of tape material 4. In a further embodiment, the position of the temporary securing points 10 can be modified relative to the center of rotation of the anvil 8, thereby allowing variation of the length of the desired length of tape material 4.

Since, the apparatus 100 utilizes continuous rotary motion as opposed to reciprocating motion, compared to most of the prior art, it requires low maintenance. The apparatus 100 is also of a simple design compared to the prior art, also making it cheap to manufacture, run and maintain.

Those skilled in the art will recognize other suitable materials of construction and obvious alternatives for all aspects of the present invention. Those skilled in the art will also recognize suitable software and electronic control means necessary for the correct operation of all aspects of the apparatus 100.

Method of Operation

FIG. 3 shows a series of steps for placing a desired length of tape material 4, fed as a moving continuous strip of tape material 1, onto a moving continuous web of material 3, wherein the orientation of the placed desired length of tape material 4 is substantially perpendicular to the direction of movement of the moving continuous web of material 3.

A desired length of tape material 4 is provided in a first direction 15, which is substantially perpendicular in orientation to the movement of a moving continuous web of material 3 moving in a second direction. Preferably the desired length of tape material 4 is presented on an anvil 8 as herein described, wherein it is removably secured at each end by temporary securing points 10. Preferably, the temporary securing points 10 comprise one or more vacuum ports 25 such that the desired length of tape material 4 is removably secured by vacuum suction.

The paddle 2 rotates about an axis 5. The paddle 2 rotates such that the transfer surface of the paddle 6 is brought into contact with a first surface 18 of the desired length of tape material 4. The desired length of tape material 4 is then removably secured to the transfer surface of the paddle 6. Preferably, the transfer surface of the paddle 6 comprises one or more vacuum ports 22 such that the desired length of tape material 4 is removably secured by vacuum suction.

In one embodiment, the desired length of tape material 4 is presented in a first direction 15 by an anvil 8, wherein the desired length of tape material 4 is removably secured by temporary securing points 10 comprising vacuum ports 25. Therefore, in this embodiment the desired length of tape material 4 is removably secured by vacuum suction. The desired length of tape material 4 is removably secured on one side only. Preferably it is removably secured to the temporary securing points 10 on the first side 18, which is the same side that is removably secured to the transfer surface of the paddle 6. Therefore, during the transfer process only one side of the desired length of material 4 is handled by the apparatus 100.

In one embodiment, the vacuum suction holding the desired length of tape material 4 on the temporary securing points 10 is overcome by the lateral force exerted on the desired length of tape material 4 by the rotating paddle 2. Thus, the desired length of tape material 4 is transferred to the transfer surface of the paddle 6 where it is removably secured by vacuum suction. In another embodiment, the vacuum exerted by the paddle transfer surface 6 is greater than that exerted by the temporary securing points 10, to ensure the transfer of the desired length of tape material 4 onto the transfer surface of the paddle 6. In another embodiment, transfer of the desired length of tape material 4 is achieved by reducing the strength of vacuum suction exerted by the anvil temporary securing points 10 and/or simultaneously increasing the strength of vacuum suction exerted by the transfer surface of the paddle 6 at the point of transfer. In a further embodiment, transfer of the desired length of tape material 4 is achieved by switching off the vacuum suction exerted by the anvil temporary securing points 10 at the point of transfer. Other non-limiting methods of ensuring transfer from the temporary securing points 10 to the transfer surface of the paddle 6 will be recognized by those skilled in the art.

Once the desired length of tape material 4 is removably secured to the paddle transfer surface 6, the paddle 2 continues to rotate about the axis 5, such that a second side 19 of the desired length of tape material 4 is brought into contact with the moving continuous web of material 3. Preferably, the second side 19 of the desired length of tape material 4 comprises an adhesive or other means to secure the desired length of tape material 4 to the moving continuous web of material 3. In one embodiment, the attractive force between the desired length of tape material 4 and the moving continuous web of material 3 caused by the adhesive on the second side 19 of the desired length of tape material 4, is strong enough to overcome the attractive force between the desired length of tape material 4 and the transfer surface of the paddle 6 caused by the vacuum ports. In this embodiment the tape adhesion force is strong enough to overcome the vacuum suction exerted by the paddle transfer surface 6. Thus the desired length of tape material 4 is transferred from the transfer surface of the paddle 6 onto the moving continuous web of material 3. In another embodiment the strength of vacuum suction exerted by the transfer surface of the paddle 6 is reduced in order to lower the level of tape adhesive strength required to overcome the paddle vacuum at the point of transfer of the desired length of tape material 4 from the paddle transfer surface 6 to the moving continuous web of material 3. In another embodiment, the vacuum suction exerted by the transfer surface of the paddle 6 is switched off at the point of transfer of the desired length of tape material 4 from the paddle transfer surface 6 to the moving continuous web of material 3.

Preferably, the tangential velocity of the rotating paddle is substantially equal to the surface velocity of the moving continuous web of material 3, at the point the tape material is transferred from the paddle transfer surface 6 to the moving continuous web of material 3.

To transfer the desired length of tape material 4 from the paddle transfer surface 6 to the moving continuous web of material 3, a transfer gap 21 between the paddle transfer surface 6 and the moving continuous web of material 3, at the point of transfer, should be equal to or less than the thickness of the desired length of tape material 4.

To ensure a good bond between the desired length of tape material 4 and the moving continuous web of material 3, the adhesive substance should provide a bond strength of between 4 N and 20 N as measured using the American Society for Testing and Materials International (ATSM International) test ASTM D3330/D3330M—04 Standard Test Method for Peel Adhesion of Pressure-Sensitive Tape.

In the context of the present invention, "high product through-put" means greater than 250 products per minute. The apparatus 100 of the present invention can maintain a product throughput range from 1 product per minute to 1000 products per minute, preferably from 350 products per minute to 1000 products per minute, most preferably from 500 products per minute to 1000 products per minute.

Those skilled in the art will recognize that the frequency of placement of desired lengths of tape material 4 can be governed by adjusting the rotational speed of the anvil 8 and/or the speed of movement of the moving continuous web of material 3. Those skilled in the art will know how to make this adjustment to obtain the required frequency of attachment of the desired lengths of tape material 4 onto the moving continuous web of material 3. Those skilled in the art will also recognize that the frequency of transfer can be altered by adjusting the rotational speed of the paddle 2. The rotational speed of the paddle 2 can be either variable or linear during a 360° paddle rotation. Therefore, when the moving continuous strip of tape material 1 and the moving continuous web of material 3 are moving at matched speeds, the frequency of attachment is not governed by the length of the desired length of tape material 4. Those skilled in the art will also recognize suitable software and electronic control means necessary for the correct operation of all aspects of the apparatus 100.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for transferring a desired length of tape material from a moving continuous strip of tape material being fed in a first direction, to a moving continuous web of material moving in a second direction, comprising the steps of;

providing the desired length of tape material in a first direction;

rotating a paddle about an axis so that a first side of the desired length of tape material is brought into contact with a transfer surface of the paddle;

removably securing the first side of the desired length of tape material to the transfer surface of the paddle;

further rotating the paddle comprising the first side of the desired length of tape material being removably secured to the transfer surface of the paddle, about the axis, so that a second side of the desired length of the tape material is brought into contact with the moving web of material;

unsecuring the first side of the desired length of tape material from the transfer surface of the paddle;

wherein the first direction is oriented at an angle of 90°+/−30° with respect to that of the second direction;

wherein the desired length of tape material is presented in a first direction on an anvil, the anvil comprising an axis around which it rotates and a number of temporary securing points; and wherein the axis of rotation of the paddle is oriented at an angle of 90°+/−30° with respect to the axis of rotation of the anvil.

2. The process of claim 1, wherein the tangential velocity of the rotating paddle is substantially equal to the surface velocity of the moving continuous web of material, at the point the desired length of tape material is transferred from the paddle transfer surface to the moving continuous web of material.

3. The process of claim 1, wherein the second side of the desired length of tape material comprises an adhesive substance.

* * * * *